(12) United States Patent
Alexandrov

(10) Patent No.: US 9,047,503 B2
(45) Date of Patent: Jun. 2, 2015

(54) SYSTEM AND METHOD FOR AUTOMATED BIOLOGICAL CELL ASSAY DATA ANALYSIS

(75) Inventor: Yuriy Alexandrov, Cardiff (GB)

(73) Assignee: GE HEALTHCARE UK LIMITED, Buckinghamshire (GB)

( * ) Notice: Subject to any disclaimer, the term of this patent is extended or adjusted under 35 U.S.C. 154(b) by 143 days.

(21) Appl. No.: 13/811,399

(22) PCT Filed: Jul. 22, 2011

(86) PCT No.: PCT/EP2011/062630
§ 371 (c)(1),
(2), (4) Date: Jan. 22, 2013

(87) PCT Pub. No.: WO2012/010691
PCT Pub. Date: Jan. 26, 2012

(65) Prior Publication Data
US 2013/0121557 A1     May 16, 2013

(30) Foreign Application Priority Data

Jul. 22, 2010  (GB) .................................. 1012297.6

(51) Int. Cl.
*G06K 9/00* (2006.01)
*G06T 7/00* (2006.01)
(Continued)

(52) U.S. Cl.
CPC ............ *G06K 9/00147* (2013.01); *G06F 19/18* (2013.01); *G06F 19/20* (2013.01); *G06T 7/0014* (2013.01); *G06T 2207/30024* (2013.01)

(58) Field of Classification Search
USPC ......... 382/100, 128, 133, 134, 181, 190, 195; 128/922; 377/10, 11; 356/39; 348/135, 348/169–172
See application file for complete search history.

(56) References Cited

U.S. PATENT DOCUMENTS

| | | | |
|---|---|---|---|
| 4,343,782 A * | 8/1982 | Shapiro .......................... 435/7.2 |
| 6,219,440 B1 | 4/2001 | Schaff et al. |
| 6,251,616 B1 * | 6/2001 | Barbera-Guillem et al. 435/7.24 |

(Continued)

FOREIGN PATENT DOCUMENTS

WO    WO 02/099736     12/2002

OTHER PUBLICATIONS

Loew, L., et al., Trends in Biotechnology, 19:10 (2001) 401-406.
(Continued)

*Primary Examiner* — Anand Bhatnagar
(74) *Attorney, Agent, or Firm* — Sutherland Asbill & Brennan LLP

(57) ABSTRACT

In one aspect, the present invention relates to a system 100 for automated cellular assay data analysis. The system 100 comprises a virtual assay module (VAM) 115 operable to generate simulated images of cell responses to one or more stimuli. The system 100 also comprises a comparator module 116 operable to compare the actual and simulated images, and an analysis module 117 operable to quantify the differences between phenotypes represented by the actual and simulated images. Various aspects and embodiments of present invention may account for stochastic variations in the response of single cells, to provide additional useful information relating to, for example, toxological effects and/or for use as part of a feedback mechanism to refine dynamically a virtual assay model such that it is not limited by way of there being only inadequate static fitting expressions available.

15 Claims, 17 Drawing Sheets

(51) Int. Cl.
G06F 19/18 (2011.01)
G06F 19/20 (2011.01)

(56) References Cited

U.S. PATENT DOCUMENTS

| 7,279,338 | B2* | 10/2007 | Kim et al. | 436/177 |
|---|---|---|---|---|
| 2002/0164063 | A1* | 11/2002 | Heckman | 382/133 |
| 2003/0018457 | A1* | 1/2003 | Lett et al. | 703/11 |
| 2005/0074745 | A1* | 4/2005 | Clayton et al. | 435/4 |
| 2006/0050946 | A1* | 3/2006 | Mitchison et al. | 382/133 |
| 2008/0050756 | A1* | 2/2008 | Kim et al. | 435/7.21 |
| 2009/0028413 | A1* | 1/2009 | Goodwin et al. | 382/133 |

OTHER PUBLICATIONS

Slepchenko, B., et al., Annual Review of Biophysics and Biomolecular Structure, 31 (2002) 423-441.
Walker, D., et al., BMC Systems Biology, 2:1 (2008) 102.
Zhao, T., et al., Cytometry Part A., 71A:12 (2007) 978-990.

* cited by examiner

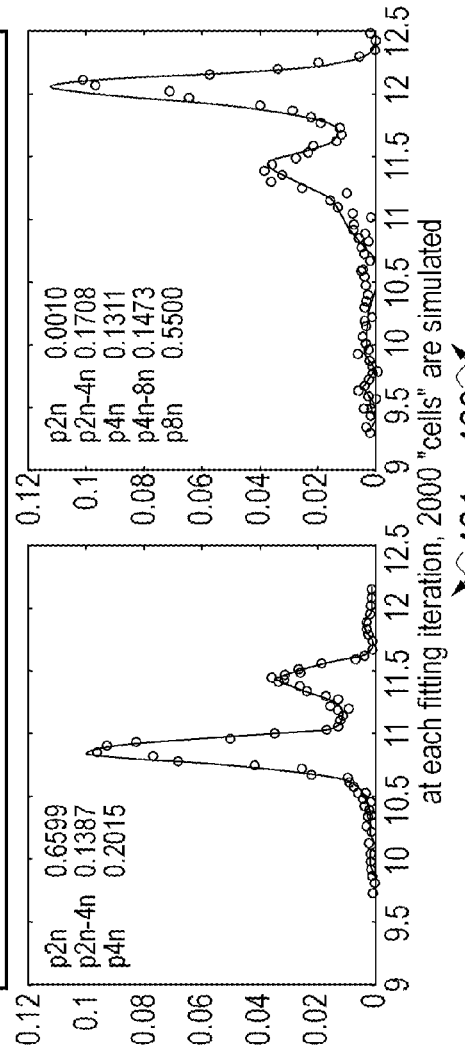

integrated nuclear intensity (J) histograms analysis of cell cycle phases in mixed population by total nuclear fluorescence (J) histograms model DNA content (a) by mixture distribution with weights $p_{2n}, p_{2n-4n}, p_{4n}$ (cellular event is an occurrence of a cell characterized by 3 possible outcomes G1, S, and G2/M) ($p_{2n} + p_{2n-4n} + p_{4n} = 1$, etc.)

$$P_{2n4n}(a) = p_{2n} \cdot \delta(a-1) + p_{2n-4n} \cdot Box(1,2) + p_{4n} \cdot \delta(a-2)$$

analogously for the case with polyploids:

$$P_{2n4n8n}(a) = p_{2n} \cdot \delta(a-1) + p_{2n-4n} \cdot Box(1,2) + p_{4n} \cdot \delta(a-2) + p_{4n-8n} \cdot Box(2,4) + p_{8n} \cdot \delta(a-4)$$

$$J = \sum_{nucleus} Intensity \sim N_{fluorescent\ molecules} \sim a$$

$$J = J_0 a^\gamma \cdot (1+\eta), \quad \eta \sim G(0, \sigma_\eta) \quad \text{(measurement model)}$$

at each fitting iteration, 2000 "cells" are simulated

FIG. 4

SYSTEM AND METHOD FOR AUTOMATED BIOLOGICAL CELL ASSAY DATA ANALYSIS

CROSS-REFERENCE TO RELATED APPLICATIONS

This application is a filing under 35 U.S.C. 371 of international application number PCT/EP2011/062630, filed Jul. 22, 2011, published on Jan. 26, 2012 as WO 2012/010691, which claims priority to application number 1012297.6 filed in Great Britain on Jul. 22, 2010.

FIELD

The present invention relates generally to a system and method for automated biological cellular assay data analysis.

BACKGROUND

Various systems and methods for analysing biological cell assay images exist. Some can be made automated or semi-automated to aid scientists in identifying desirable phenotype responses to certain stimuli, such as drug compounds, in high-throughput screening (HTS) applications.

For example, various methods may be used to apply curve fitting to fit measured cell phenotype data to a mathematical model or expression in order to try and obtain parameters indicative of cellular response to various stimuli to aid in drug discovery [1]. Various other methods use comparisons of real and modelled image data in an attempt to quantify various biological phenotypes, such as spatiotemporal evolution of a given biological or physiological system [2, 3].

However whilst such known techniques are useful for limited sets of circumstances, there is not only a danger of inadequate phenomenological fitting expressions being available to accurately model the assays, but these techniques also generally cannot provide certain important biological data because they rely on averaged measured phenotype responses such as whole field-of-view (FOV) images, for example.

SUMMARY OF THE INVENTION

Various aspects and embodiments of the present invention have thus been devised bearing in mind the disadvantages of conventional techniques and with a view to improving the quantifiable cell phenotype information that can be automatically extracted from actual cell images.

According to a first aspect of the present invention, there is thus provided a system for automated cellular assay data analysis. The system comprises a virtual assay module (VAM) that is operable to generate simulated images of cell responses to one or more stimuli. The system also comprises a comparator module that operable to compare the actual and simulated images, and an analysis module that is operable to quantify the differences between phenotypes represented by the actual and simulated images.

According to a second aspect of the present invention, there is provided a method for automated biological cell assay data analysis. The method comprises acquiring one or more actual cell images, creating one or more virtual assay model images, comparing at least one of the actual cell images to at least one of the virtual assay model images, and quantifying any differences identified by comparing actual and virtual assay model images to provide at least one difference parameter.

Various aspects and embodiments of present invention may account for stochastic variations in the response of single cells, to provide additional useful information relating to, for example, toxological effects and/or for use as part of a feedback mechanism to refine dynamically a virtual assay model such that it is not limited by way of there being only inadequate static fitting expressions available.

In contrast, when using conventional techniques which imply synchronous multi-cell reactions (i.e. where individual cells all act substantially simultaneously and in substantially the same way), it would be extremely difficult to account for any variations in the responses of individual cells, not least because of the large amount of tracking data that would be needed.

BRIEF DESCRIPTION OF THE DRAWINGS

FIG. 4 shows a further technique for analysing differences between phenotypes represented by actual and simulated images in accordance with an embodiment of the present invention;

DETAILED DESCRIPTION

Figure 1:
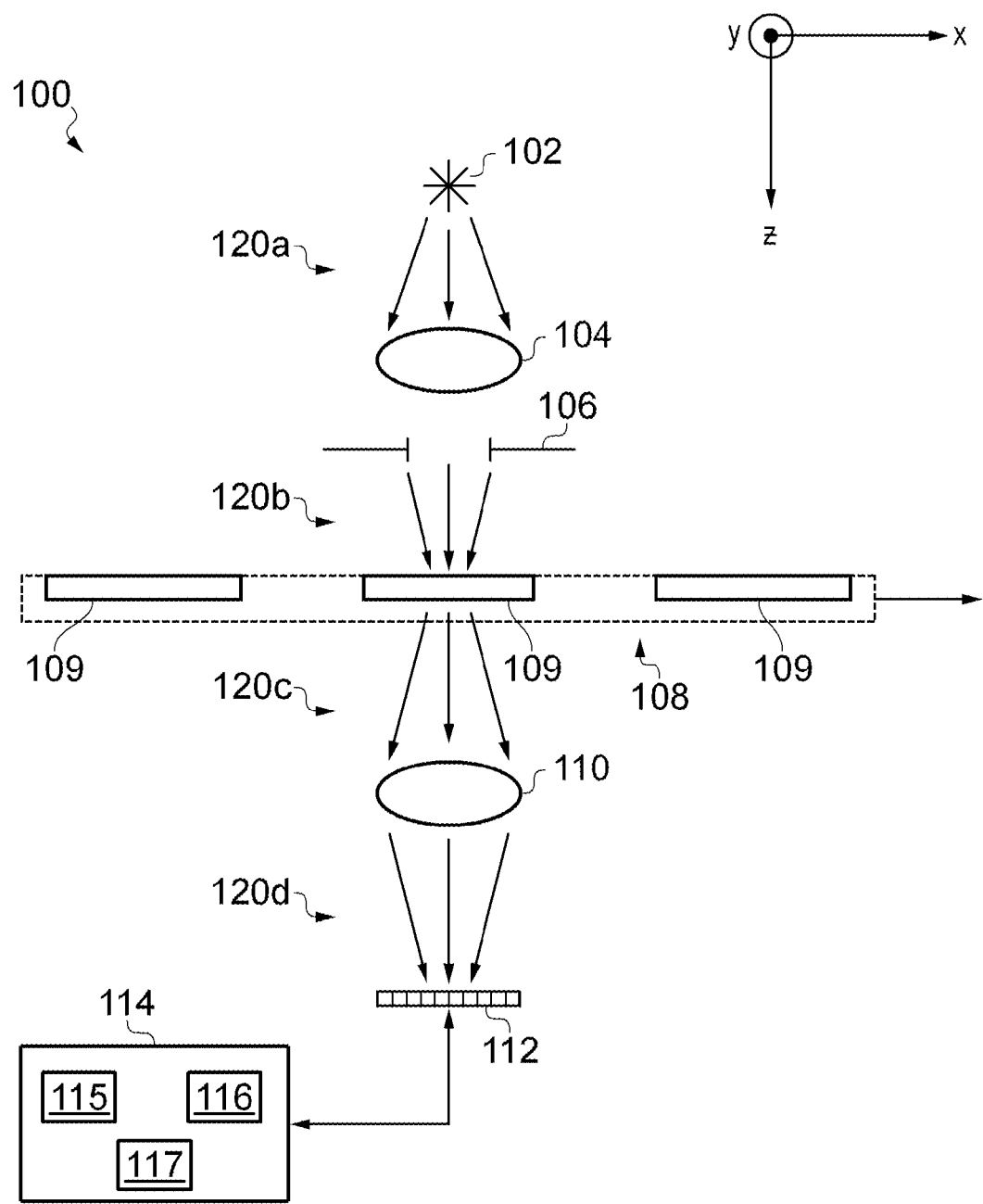
FIG. 1 shows a system for automated cellular assay data analysis in accordance with an embodiment of the present invention.

FIG. 1 shows a system 100 for automated cellular assay data analysis in accordance with an embodiment of the present invention. Cellular assay data analysis may, for example, be used for toxological screening of pharmacological compounds by quantifying one or more phenotypes, such as cytoplasmatic membrane integrity, seen in images of treated cells. The system 100 may also be used, for example, for automated high-content screening (HCS) and/or high-throughput screening (HTS).

The system 100, which is illustrated schematically for clarity, comprises a light source 102 for producing light 120a. The light 120a is focussed by a condenser 104 onto a test plate 108. The test plate 108 may contain an array of wells or spots 109 to be imaged. The condenser 104 can focus the light 120b in a focal plane at the test plate 108. The test plate 108 may be provided as a consumable product, and the spots 109 might contain various materials that are able to interact with certain types of cells (e.g. mammalian cells).

In various embodiments, the test plate 108 may comprise at least one fiducial marker (not shown) provided to aid in aligning the test plate 108 within the system 100. For example, one or more coloured dyes may be provided within the spots 109. Such coloured dyes can be identified by various imaging systems in order to derive data relating to the relative positioning of the test plate 108 within the system 100. For example, the system 100 may include a GE IN-Cell Analyzer 1000 that is commercially available from GE Healthcare Life Sciences, Little Chalfont, Buckinghamshire, U.K., and which can use four colour channels to image the test plate 108. One colour channel may thus be dedicated to imaging coloured fiducial markers provided in various of the spots 109 in order to obtain data relating to the positioning of the test plate 108 within the system 100.

The system 100 also contains a detector system 112 and a translation mechanism (not shown). The translation mechanism is configured to move the focus of the light 120b relative to the test plate 108 (e.g. by moving the test plate 108 in the x-y plane). This enables a plurality of actual images to be acquired from respective of the individual spots 109. Additionally, the translation mechanism may also be operable to move the test plate 108 in the z-direction shown in FIG. 1, for example, in order to bring the spots 109 into focus.

For certain embodiments, only one spot is imaged at a time. The images acquired are of sufficient magnification to resolve cells and sub-cellular morphology. With the current GE IN-Cell Analyzer 1000, this may entail use of a 20× objective, the field of view of which is slightly smaller than a single spot. However, various methods of the invention would also work for lower power magnification imaging, e.g. on GE IN-Cell Analyzer 1000 using a 4× objective to image 4-6 spots/image.

An aperture stop 106 is optionally provided between the light source 102 and the detector system 112, the size of which may be variable. For example, various differently sized movable apertures may be rotated into position or a continuously variable iris-type diaphragm may be provided. Image contrast can be controlled by changing the aperture setting of the aperture stop 106.

Focussed light 120b passing through the aperture stop 106 passes through the sample test plate 108 in a transmission imaging mode. Emergent light 120c modulated with image information relating to material adjacent to an individual spot 109 is collected by an objective lens 110 and focussed 120d onto the detector system 112, and is used to form an original image for that spot 109.

Various embodiments of methods of the present invention are independent of the imaging modality used, e.g. they can operate with transmission or reflection geometry. For GE IN-Cell Analyzer 1000 imaging an epi-fluorescence mode may be used, with both the fiducial marker spots and the assay signals from the cells being imaged at different excitation and emission wavelengths. However there is nothing in principle to prevent a mix of imaging modes being deployed, provided that they do not interfere. For example, it would be possible to use a non-fluorescent dye for fiducial marking and to detect the fiducial marks by absorbance in reflectance or transmission geometry, while detecting assay signals by epi-fluorescence.

The detector system 112 is operable to acquire a plurality of images from the test plate 108. For example, images may be obtained each representing different spots 109 or of the same spot 109 at different points in time. Differences between neighbouring spots 109 or temporal changes occurring within the same spot 109 can thus be analysed.

The detector system 112 is also operably coupled to a processor 114 that in turn is operable to process the images. Analysis of the images may be used to provide for toxicological screening. Of course, such images may be generated by the system 100 itself or might be provided from storage and/or transmitted to the processor 114 from a remote location (not shown).

The processor 114 is configured to provide a virtual assay module (VAM) 115 for generating simulated images of cell responses to various agents, a comparator module 116 for comparing the actual and simulated images, and an analysis module 117 for quantifying the differences between the actual and simulated images and adjusting the VAM in accordance with any such quantified differences.

The analysis module 117 is further operable to provide feedback to adjust the VAM 115 in accordance with the quantified differences such that the phenotypes of the actual and simulated images converge, and to quantify temporally the differences between the phenotypes represented by the actual and simulated images. This permits the analysis module 117 to determine a response or time-dependent cell/multi-cell reaction to application of a stimulus (such as, for example, a drug treatment etc.). Moreover, by enabling temporal quantification of phenotype responses, responses produced by different techniques (e.g. different fluorescent markers) are made directly comparable thus allowing an interpretation of causality to be obtained.

In this embodiment, the analysis module 117 is further operable to apply stochastical fitting to quantify one or more response properties of at least one single cell's response to the application of one or more stimuli. This further enables the analysis module 117 to quantify a multi-cellular system's heterogeneity during the response using a heterogeneity measurement parameter.

Various embodiments of FIG. 1 can be used to provide phenomenological response fitting for a high-throughput screening (HTS) analysis. In one example, the phenotypes are toxological phenotypes and the quantified differences are indicative of stimuli toxicity. For example, HTS may be used to automatically analyse the actual images to quantify the amounts and/or types of cell membrane disruptions, micronuclei, etc., in order to indicate the relative toxicity of a candidate drug stimulus. Rapid and accurate automated HTS can thereby be provided to identify target non-toxic drug compounds warranting further scientific investigation.

Additionally, the processor 114 can be configured to control the translation mechanism (not shown) to move the focal position of the light source 102 relative to the spot plate 108. The processor 114 may, for example, be provided as part of a conventional computer system appropriately programmed to implement one or more of the VAM module 115, the comparator module 116 and the analysis module 117, or may be provided by a digital signal processor (DSP), dedicated application specific integrated circuit (ASIC), appropriately configured firmware, etc.

As discussed above, various embodiments of the invention may be used to automatically screen cells, for example, in order to detect and quantify specific events that are indicative of drug toxicity. Such improved automated screening can thereby reduce the need to test various compounds on human or animal models by identifying only those candidates having the lowest amount of toxicity specific phenotypes.

In certain embodiments, the system 100 as described above may be used to implement the following method that is described below in connection with FIG. 2.

Figure 2:
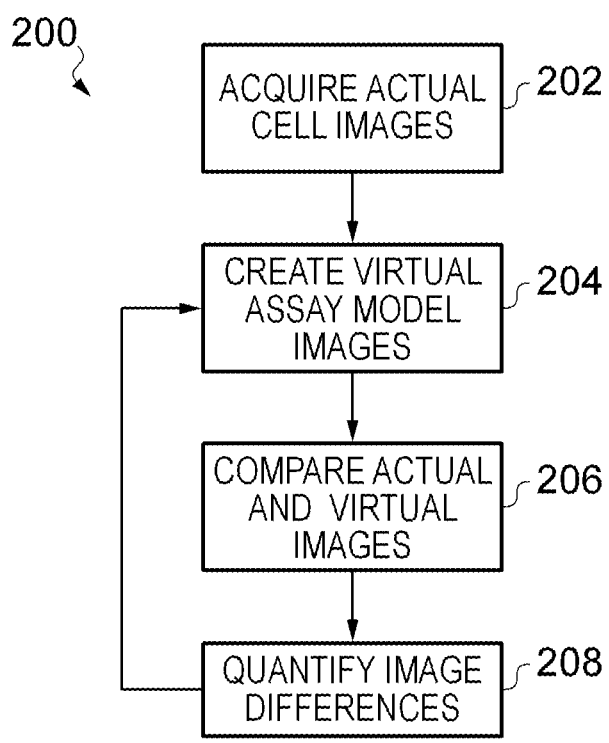
FIG. 2 shows a flowchart depicting a method in accordance with various embodiments of the present invention.

FIG. 2 shows a flowchart depicting a method 200 that may be used in accordance with various embodiments of the present invention. The method 200 is for automated biological cell assay data analysis, and various more detailed examples are described below for illustrative purposes in connection with toxicology analysis.

At step 202 the method 200 comprises acquiring one or more actual cell images. The actual cell images may be acquired using, for example, a HTS or may include one or more stored images previously acquired locally and/or remotely. For example, actual cell images can be generated at remote locations and transmitted to a central image processing facility, possibly via the Internet using a secured data link or virtual private network (VPN).

At step 204 the method 200 comprises creating one or more virtual assay model images. The virtual assay model images can be created using a stochastic model, i.e. a model that simulates a stochastic process whose behaviour is non-deterministic in that a next system state is determined both by the process's predictable events and by a random element.

Various embodiments apply stochastic simulation techniques to the analysis of time-dependent responses in cellular assays. In simulations, cellular assays can be treated as a statistical ensemble composed of many random dynamic cellular events. The preferred method uses a procedure of stochastically driven fitting for estimating the properties of a single cell's response, as well as assessing a cellular system's heterogeneity during the response.

The assay response of a single cell is described in various terms such as time (duration), amplitude (extent) responses, and the distribution of the response starting times (e.g. the centre and margins of the distribution). The advantage of the temporal description is that it makes responses registered by different measurement tools (e.g. different fluorescent markers) immediately comparable, thereby allowing an interpretation of causality (e.g. for early/late reactions indicating the preceding and subsequent cellular processes). When stochastic techniques are not used, such a method can be reduced to the fitting of a response to a phenomenological time-dependent expression.

At step 206 the method 200 comprises comparing at least one of the actual cell images to at least one of the virtual assay model images. Various techniques may be used, such as for example least squares fitting, entropy based techniques, etc. [2, 4].

At step 208 the method 200 comprises quantifying any differences identified by comparing (206) actual and virtual assay model images to provide at least one difference parameter. The difference parameter may, for example, correspond to the minimum value obtained when performing a least squares fit, entropy optimisation, etc. [2, 4] and can be used temporally quantify the differences between the phenotypes represented by the actual and virtual assay model images, for example, in single cells and/or for responses generated by collections of such cells (e.g. as quantified by a heterogeneity measurement parameter).

Having obtained a suitable difference parameter, the virtual image model can be modified in dependence thereon and an new set of one or more virtual assay model images recreated said using the modified virtual image model. This enables the method 200 to iteratively provide feedback to adjust the virtual assay model so as to minimise the values of the difference parameter in order that the phenotypes of the actual and virtual assay model images converge. Hence a virtual assay can be provided that uses stochastic simulation and phenomenological response fitting suitable for HTS analyses.

Various embodiments of the method 200 may be implemented in one or more of hardware, software and firmware. For example, a system of the type described above in connection with FIG. 1 may be used, or software upgraded, for such a purpose.

For example, the method enables the provision of a quantitative software package that can combine one or more of the following functions: a) a dynamic description of a single cell transient response including its modelling and representation; b) stochastic simulations; and c) fitting and parameter estimation. Such a software package enables the generation of a flexible model of assay response and the comparison of simulated and measured data. The proposed technique may also be used without data fitting, to generate a "virtual assay" i.e. a simulation describing a cellular response. Such simulations might be arranged according to a hypothetical mechanism describing the action of any potential stimulus and thereby used to predict various complex system responses.

Various examples describing various real-life responses obtained using the mitochondrial marker TMRM will now be given. In actual images of cells stained with TMRM, the level of fluorescence intensity is related to the mitochondrial membrane potential, loss of which can be an indicator of cytotoxicity.

The toxicity assays used well plate bio-microscopy imaging to obtain actual cell images, using fluorescent markers and a GE IN-Cell Analyzer instrument, with FOV related data.

The dynamics of a single cell toxicological response is related to the toxicological mechanism. A characteristic duration $\tau$ of the response can be an indicator of a mechanism or sub-mechanism sensed by a particular marker (e.g. fluorescent in this case). In order to estimate the time $\tau$ reliably data was sampled at a rate $\Delta t \ll \tau$. With the GE IN-Cell Analyzer acquisition can be performed at a temporal multi-scale spanning four orders of magnitude. This was defined in terms of the sampling intervals used as follows:

1) very fast $\Delta t=1$ second (e.g. for analysing ion channel dynamics)
2) fast $\Delta t=10$ s (e.g. for analysing receptor-mediated protein kinase translocation)
3) intermediate $\Delta t=100$ s (e.g. for analysing receptor-mediated Rac-1 translocation)
4) slow $\Delta t=1000$ s (e.g. for analysing gene expression)

Figure 3:
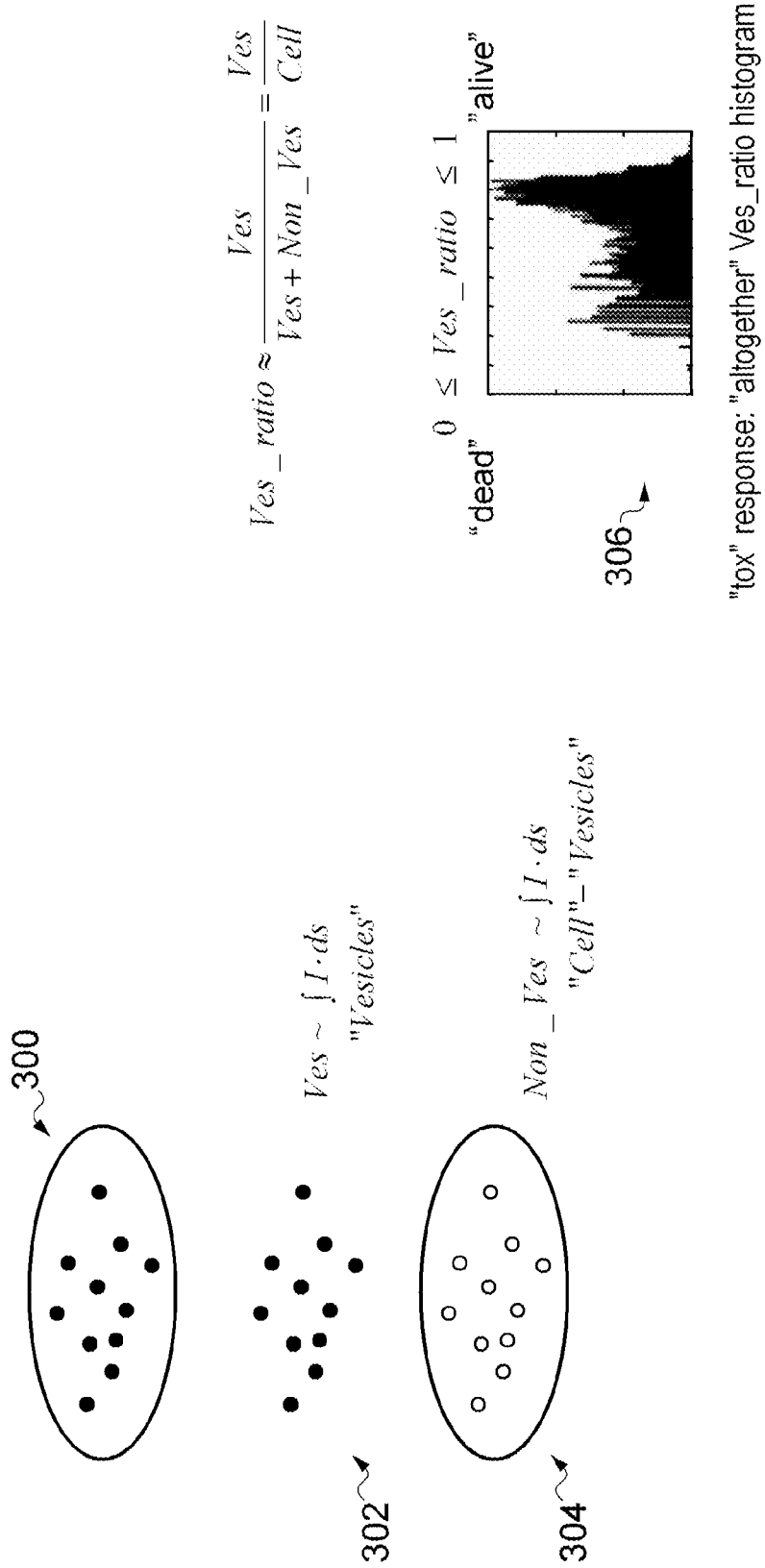
FIG. 3 shows a virtual assay model image in accordance with an embodiment of the present invention.

FIG. 3 shows a virtual assay model image 300 produced in accordance with an embodiment of the present invention. The virtual assay model image 300 shows an example of a toxicological response for cells stained with TMRM.

Live cells are characterised by a punctuate, vesicular-type, distribution of TMRM whilst dead cells, compromised cells or drug treated cells may show a uniform distribution of TMRM in the cytoplasm.

The virtual assay model image 300 thus shows a mixed distribution which is a combination of a vesicular image 302 (representing mitochondria) and a non-vesicular image 304 showing the uniform distribution of TMRM in the cytoplasm.

The total intensity if the TMRM signal in the vesicular image 302, $V_{es}$ is defined as:

$$V_{es} = \int_{vesicles} I \cdot ds \qquad \text{Equation 1}$$

where I represents a pixel intensity value and ds spatial position of pixels in the image.

The total intensity if the TMRM signal in the non-vesicular image 304, $V_{cytoplasm}$ is defined as:

$$V_{cytoplasm} = \int_{VAM\ image-vesicles} I \cdot ds \qquad \text{Equation 2}$$

From Equations 1 and 2 an relative intensity ratio $V_{es\_ratio}$ can be calculated, as follows:

$$V_{es\_ratio} \approx \frac{V_{es}}{V_{es} + V_{cytoplasm}} = \frac{V_{es}}{V_{VAM\ image}} \qquad \text{Equation 3}$$

This relative intensity ratio $V_{es\_ratio}$ is a useful parameter, in which any image proportionality factors applied are substantially cancelled out, and which can be used to measure the relative degree of mitosis in the VAM image 300, thus:

$$\text{"dead"} \ 0 \leq V_{es\_ratio} \leq 1 \ \text{"alive"} \qquad \text{Equation 4}$$

Summing across the VAM image 300, a toxicological signature response can be built up by producing a $V_{es\_ratio}$ histogram 306. Such a $V_{es\_ratio}$ histogram 306 can, for example, be used to quantify the differences between phenotypes represented by actual and simulated images, in this case when assessing toxicological responses. Hence in various embodiments phenotypes may be toxological phenotypes and the quantified differences indicative of stimuli toxicity (e.g. cell membrane disruptions, presence of micronuclei, etc.).

FIG. 4 shows a further technique for analysing differences between phenotypes represented by actual and simulated images. This technique applies a so-called "parent methodology" in which analysis is undertaken in terms of non-dynamic stochastic cellular events.

Nuclear fluorescent images 400, 402 are analysed by comparison to modelled data. Actual image 400 shows an image of diploid cells exhibiting a typical G1 S G2/M distribution, and actual image 402 an altered distribution characteristic of induced polyploidy. Both images were obtained using high throughput high content screening.

Analysis of cell cycle phases in mixed populations is performed by using total integrated nuclear fluorescence (J) histograms.

$$J = \sum_{nucleus} \text{Intensity} \sim N_{fluorescent\ moleclues} \sim a \qquad \text{Equation 5}$$

$$J = J_0 a^{\gamma} \cdot (1 + \eta), \eta \sim G(0, \sigma_{\eta}) \qquad \text{Equation 6}$$

$\eta$ being determined from a measurement model.

DNA content (a) is modelled by mixture distribution weights $p_{2n}$, $p_{2n-4n}$, $p_{4n}$ (where $p_{2n}+p_{2n-4n}+p_{4n}=1$, etc.) such that:

$$P_{2n4n}(a) = p_{2n} \cdot \delta(a-1) + p_{2n-4n} \cdot \text{Box}(1,2) + p_{4n} \cdot \delta(a-2) \qquad \text{Equation 7}$$

Analogously for the case with polyploids:

$$P_{2n4n8n}(a) = p_{2n} \cdot \delta(a-1) + p_{2n-4n} \cdot \text{Box}(1,2) + p_{4n} \cdot \delta(a-2) + p_{4n-8n} \cdot \text{Box}(2,4) + p_{8n} \cdot \delta(a-4) \qquad \text{Equation 8}$$

Graph 404 shows the modelled DNA content distribution having applied a two-thousand cell simulation at each fitting iteration. Similarly, graph 406 shows the analogous case for polyploids. These can be compared to the processed integrated nuclear fluorescence (J) histograms 408, 410 for the respective actual images 400, 402 (e.g. using known correlation measurement techniques) in order to provide a quantified measurement indicating the differences between actual and simulated images.

Figure 5:
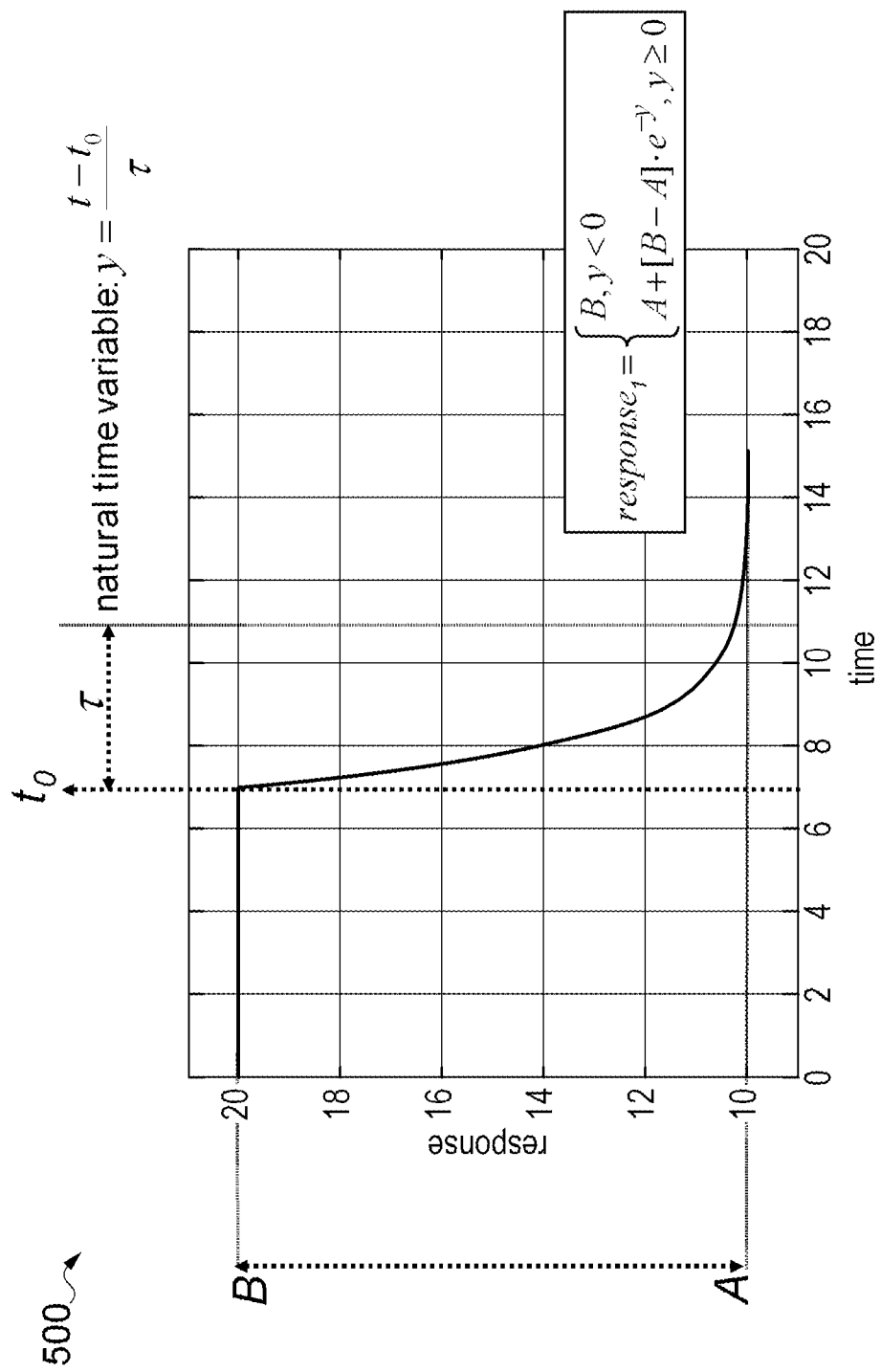
FIG. 5 shows the dynamics of a single cell toxicological response.

FIG. 5 shows the dynamics of a single cell toxicological response $\text{response}_1$ in graph 500. The toxicological response is transient and shows cell death. The transient response starts at time $t_0$, lasts for a duration $\tau$ and has an amplitude equal to B−A.

The dynamic response can be defined as:

$$\text{response}_1 = \begin{cases} B, & y < 0 \\ A + [B-A] \cdot e^{-y}, & y \geq 0 \end{cases} \qquad \text{Equation 9}$$

where natural time variable, y, is defined as $$y = \frac{t - t_0}{\tau}.$$

Figure 6:
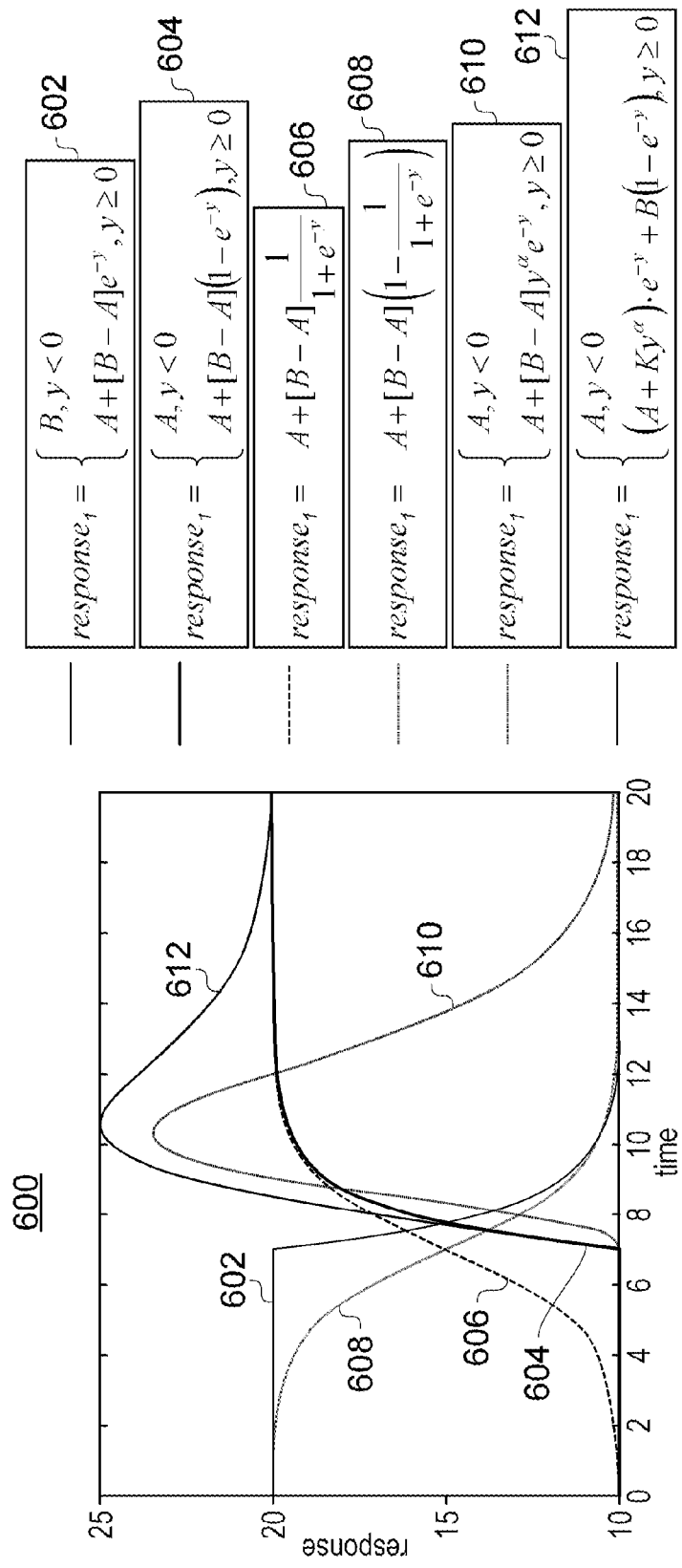
FIG. 6 shows the dynamics of various single cell transient responses.

FIG. 6 shows a graph 600 illustrating the dynamics of various possible single cell transient responses that can be modelled.

In the first response curve 602, the response is defined as per Equation 9, above.

In the second response curve 604, the response is defined as:

$$\text{response}_1 = \begin{cases} B, & y < 0 \\ A + [B-A] \cdot (1 - e^{-y}), & y \geq 0 \end{cases} \qquad \text{Equation 10}$$

In the third response curve 606, the response is defined as:

$$\text{response}_1 = A + [B-A] \cdot \left(\frac{1}{1 + e^{-y}}\right) \qquad \text{Equation 11}$$

In the fourth response curve 608, the response is defined as:

$$\text{response}_1 = A + [B-A] \cdot \left(1 - \frac{1}{1 + e^{-y}}\right) \qquad \text{Equation 12}$$

In the fifth response curve 610, the response is defined as:

$$\text{response}_1 = \begin{cases} A, & y < 0 \\ A + [B-A] \cdot y^{\alpha} e^{-y}, & y \geq 0 \end{cases} \qquad \text{Equation 13}$$

In the sixth response curve 612, the response is defined as:

$$\text{response}_1 = \begin{cases} A, & y < 0 \\ (A + Ky^{\alpha}) \cdot e^{-y} + B(1 - e^{-y}), & y \geq 0 \end{cases} \qquad \text{Equation 14}$$

These various response curves can be used to fit single cell transient responses to enable a VAM to generate simulated images of cell responses to one or more stimuli which may be fit iteratively to actual data by an analysis module, for example. This enables various embodiments of the present invention to temporally quantify the differences between the phenotypes represented by actual and simulated images.

For example, analytical expressions involving some four to six parameters defining a single cell response such as start time, duration, amplitude and shape can all be adjusted to obtain a best analytical fit.

Moreover, the response, or responses, can be made time-dependent for one or more cells, multi-cell, inter-cellular reactions, etc. to a stimulus (such as a drug treatment etc.).

Such a temporal description thereby enables responses produced by different techniques (e.g. using different fluorescent markers, or even different image modalities) to be made directly comparable, hence allowing an interpretation of causality to be obtained.

Figure 7:
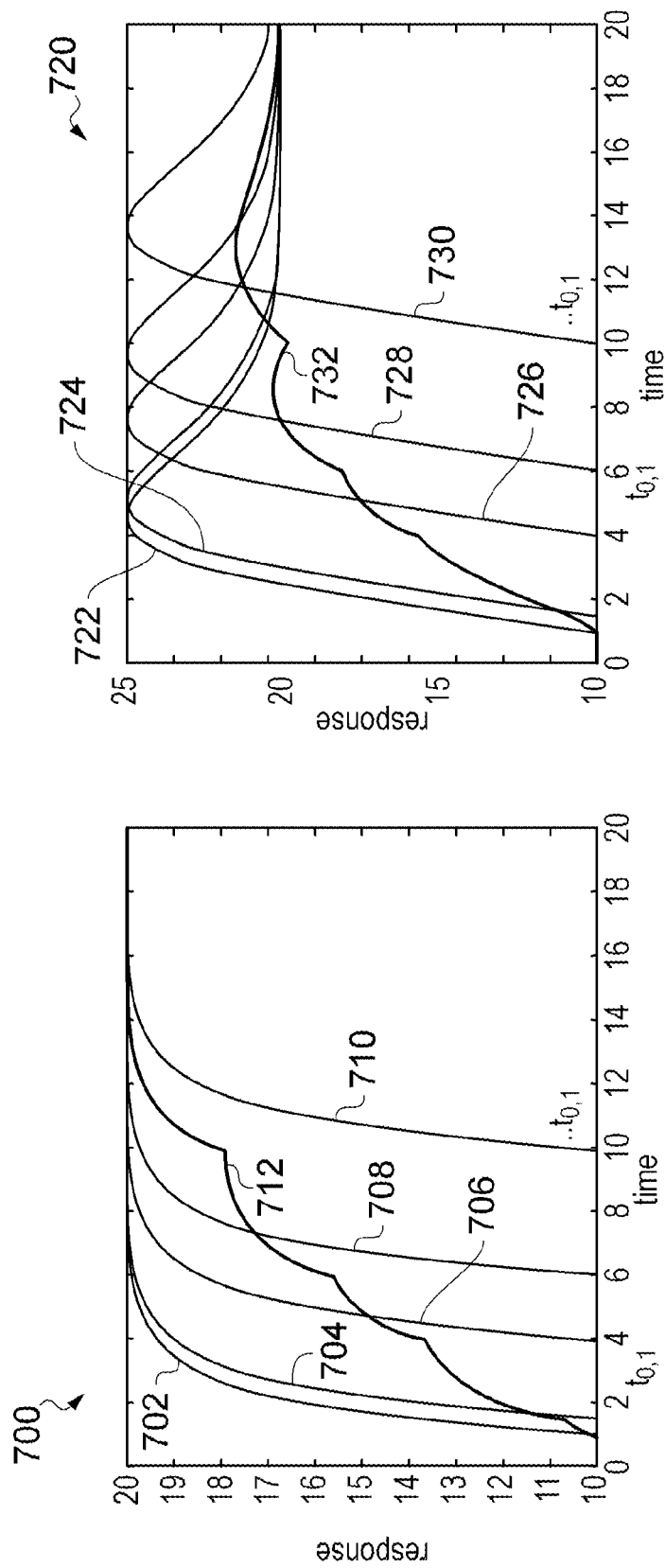
FIG. 7 shows first and second graphs showing how first and second field-of-view (FOV) averaged time-dependent assay responses are built-up.

FIG. 7 shows first and second graphs 700, 720 showing how first and second field-of-view (FOV) averaged time-dependent assay responses 712, 732 are built-up.

The responses 712, 732 are generated on the assumption that the main variability in toxicological response is due to the $t_0$ distribution. The respective FOV-averaged time dependent responses FOV_response(t) are modelled with the help of $response_1(t)$ functions using differing time shifts, thus:

$$\text{FOV\_response}(t) = \frac{1}{N_{cells}} \sum_{i=1}^{N_{cells}} [\text{response}_1(t, \ldots \mid t_{0,i}) + \eta_i] \qquad \text{Equation 15}$$

where $\eta_i$ is an optionally added measurement noise parameter.

The first FOV response 712 is built up from time shifted $response_1(t)$ functions 702, 704, 706, 708 and 710. The second FOV response 732 is built up from time shifted $response_1(t)$ functions 722, 724, 726, 728 and 730.

Figure 8:
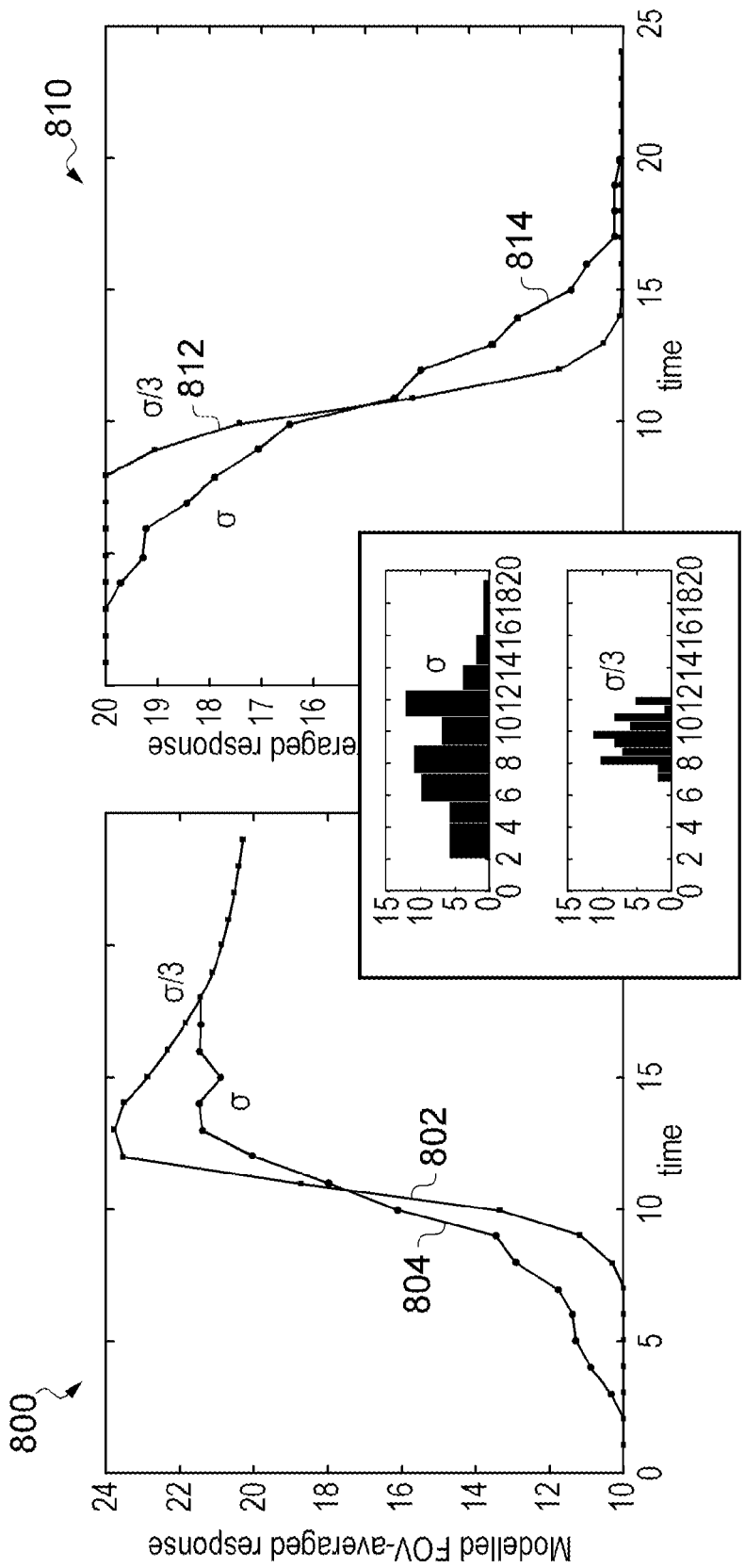
FIG. 8 shows first and second graphs showing various modelled field-of-view (FOV) averaged time-dependent assay distribution responses.

FIG. 8 shows first and second graphs 800, 810 showing modelled field-of-view (FOV) averaged time-dependent assay distribution responses 802, 804, 812, 814.

Again, the distribution responses 802, 804, 812, 814 derive from a $t_0$ distribution. The $t_0$ distribution may, for example, be uniform (i.e. a box distribution) or Gaussian in nature. The modelling technique may thus be akin to a stochastic simulation.

The first graph 800 shows a σ/3 distribution response 802 and a σ distribution response 804. These distribution responses were produced for a $response_1(t)$ function having a bell shaped rise, with $N_{cells}$=60, $\eta_i$=0 and a Gaussian distribution for $t_0$ "μ", "σ", σ>>τ).

The second graph 810 shows a σ/3 distribution response 812 and a σ distribution response 814. These distribution responses were produced for a $response_1(t)$ function having an exponential drop shape, with $N_{cells}$=60, $\eta_i$=0 and a Gaussian distribution for $t_0$ ("μ", "σ", σ>>τ).

A stochastic fitting procedure can thus be applied for estimating:

1) parameters of the distribution of the starting time $t_0$ (e.g., $\mu_{t0}$ and $\sigma_{t0}$);
2) response duration τ; and/or
3) response amplitude (B−A).

The shape of the response can be determined by studying individual cell response records, e.g. by using a cell tracking algorithm.

Figure 9:
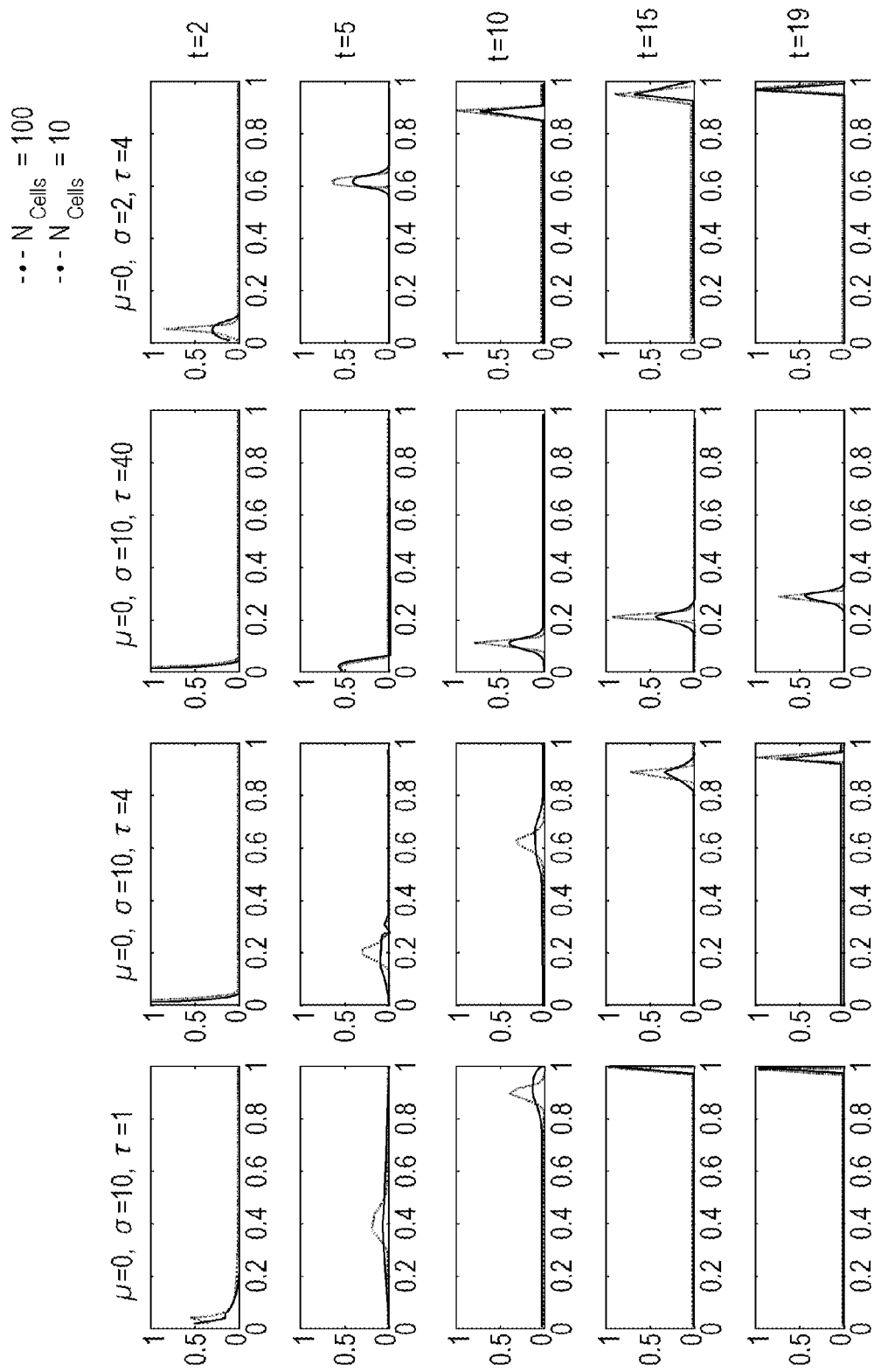
FIG. 9 shows the distribution of the FOV response at various time points.

FIG. 9 shows the distribution of the FOV response at various time points. The response distribution depends upon the mentioned parameters and the number of responding cells $N_{cells}$ imaged in the field-of-view.

The $response_1(t)$ function had an exponential rising shape and the $t_0$ distribution is uniform (i.e. box shaped). The temporal distributions are shown evolving down each depicted column for both $N_{cells}$=10 and $N_{cells}$=100 with μ=0 and σ and τ varying from column to column.

Figure 10:
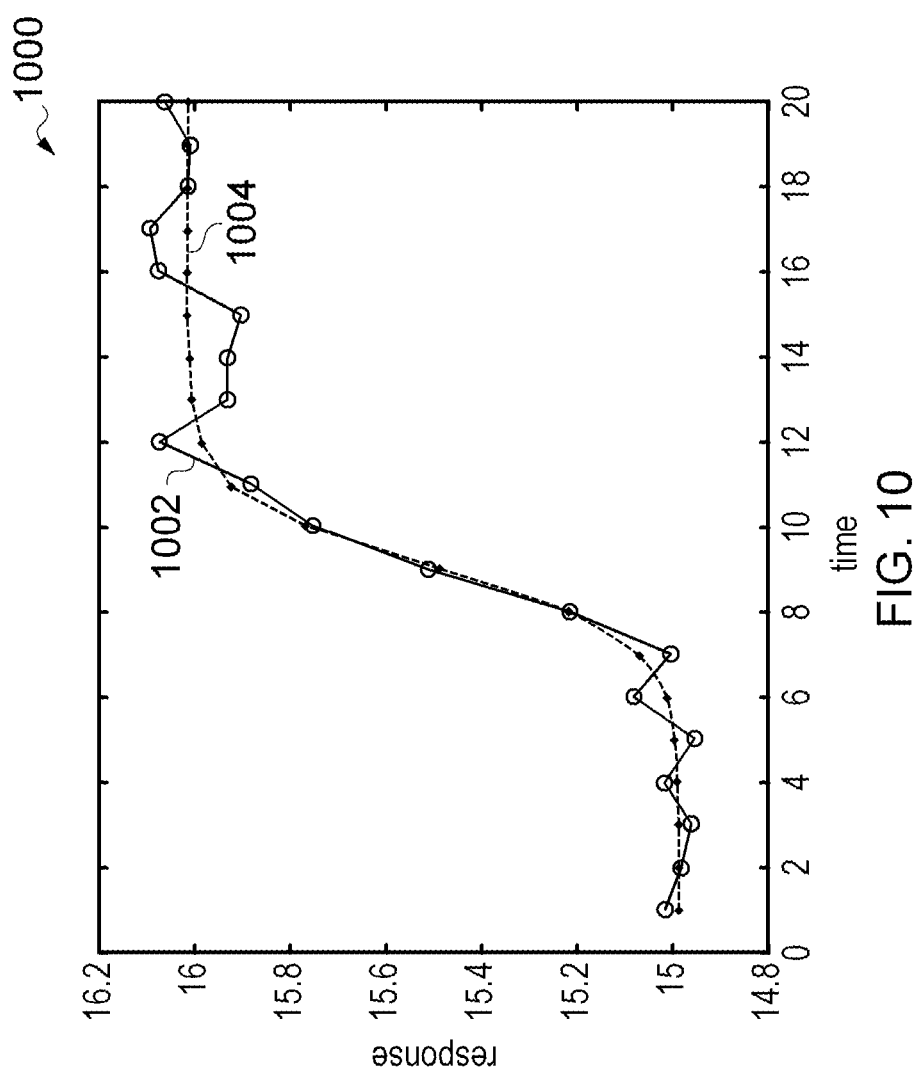
FIG. 10 shows a graph illustrating conventional direct analysis of a time-dependent response by fitting.

FIG. 10 shows a graph 1000 illustrating conventional direct analysis of a time-dependent response by fitting. Raw data 1002 is fit mathematically to the curve 1004.

Such fitting is well-understood and a classical application of computational mathematics to scientific results. However, the use of such a technique does possess the following drawbacks: a) for a single cell, cell tracking data needs to be collected on a massive scale; b) for a FOV-averaged response, the technique assumes temporally synchronous reactions of the cells; and c) there is a danger that a lack of adequate phenomenological fitting expressions are available.

Various assay response and analysis algorithms were created using MATLAB®. They included working versions of functions and procedures mentioned previously in the description.

However, in order to verify further the robustness of the developed methods, these algorithms were tested on FOV-averaged data generated from a real toxicity assay. The cell-based experiment involved the influence of several drugs and the applications of two fluorescent markers during a 5-hour time course. The general background for such an experimental study is outlined in the article by O'Brien et al [4].

FIRST EXAMPLE

The first example analyzed the cytoplasmatic membrane integrity, as indicated by the TOTO-3 marker. TOTO-3 stains cell nuclei only after cell plasma membrane disruption. The $response_1(t)$ generated by disruption to the membrane is therefore a curve representing the increase of cell nuclei intensity in TOTO-3 channel. This intensity was measured by a microscopy HTS system. However, the exact moment when a particular membrane became disrupted was unpredictable.

The analysis therefore used stochastic fitting involving a single time parameter (the width of the box-shaped distribution of starting times of the response).

Figure 11:
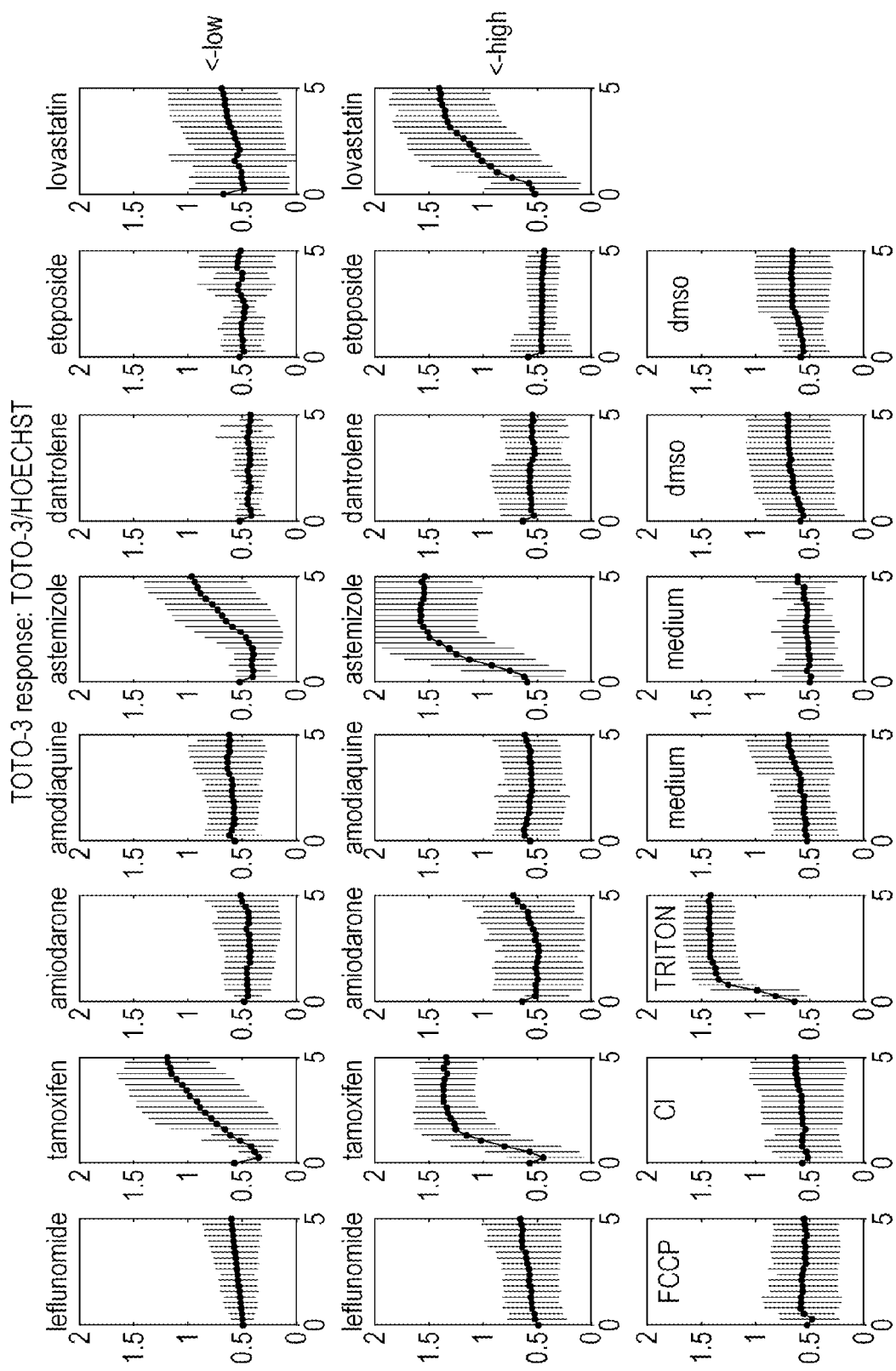
FIG. 11 shows an experimental raw TOTO-3 response.

FIG. 11 represents the raw TOTO-3 response. The TOTO-3 response was taken for two values of drug concentration, denoted "high" and "low". The bottom panel shows the response when treated with various control treatments (i.e. FCCP: p-trifluoromethoxy carbonyl cyanide phenyl hydrazone; CI: calcium ionophore A23187; Triton: Triton-X-100; Medium: culture medium; DMSO: dimethylsulphoxide).

FCCP is an uncoupler of oxidative phosphorylation in mitochondria. It is capable of depolarizing plasma and mitochondrial membranes and is therefore used as a positive control for the TMRM stain. FCCP depolarises the mitochondrial membrane resulting in a TMRM signal decrease compared to negative controls.

Calcium ionophore A23187 is highly selective for Calcium. This is a positive control for the Fluo4-AM stain. CI results in an overall increase in the intracellular Calcium levels therefore resulting in a signal increase in the Fluo4-AM intensity compared to negative controls.

The deteregent/surfactant Triton-X-1000 acts as a positive control for the TOTO-3 stain. Triton will permeabilise the cell membranes resulting in a signal increase in the TOTO-3 intensity compared to negative controls.

The culture medium acts as a negative control.

DMSO is used a drug carrier and acts as negative control.

Figure 12:
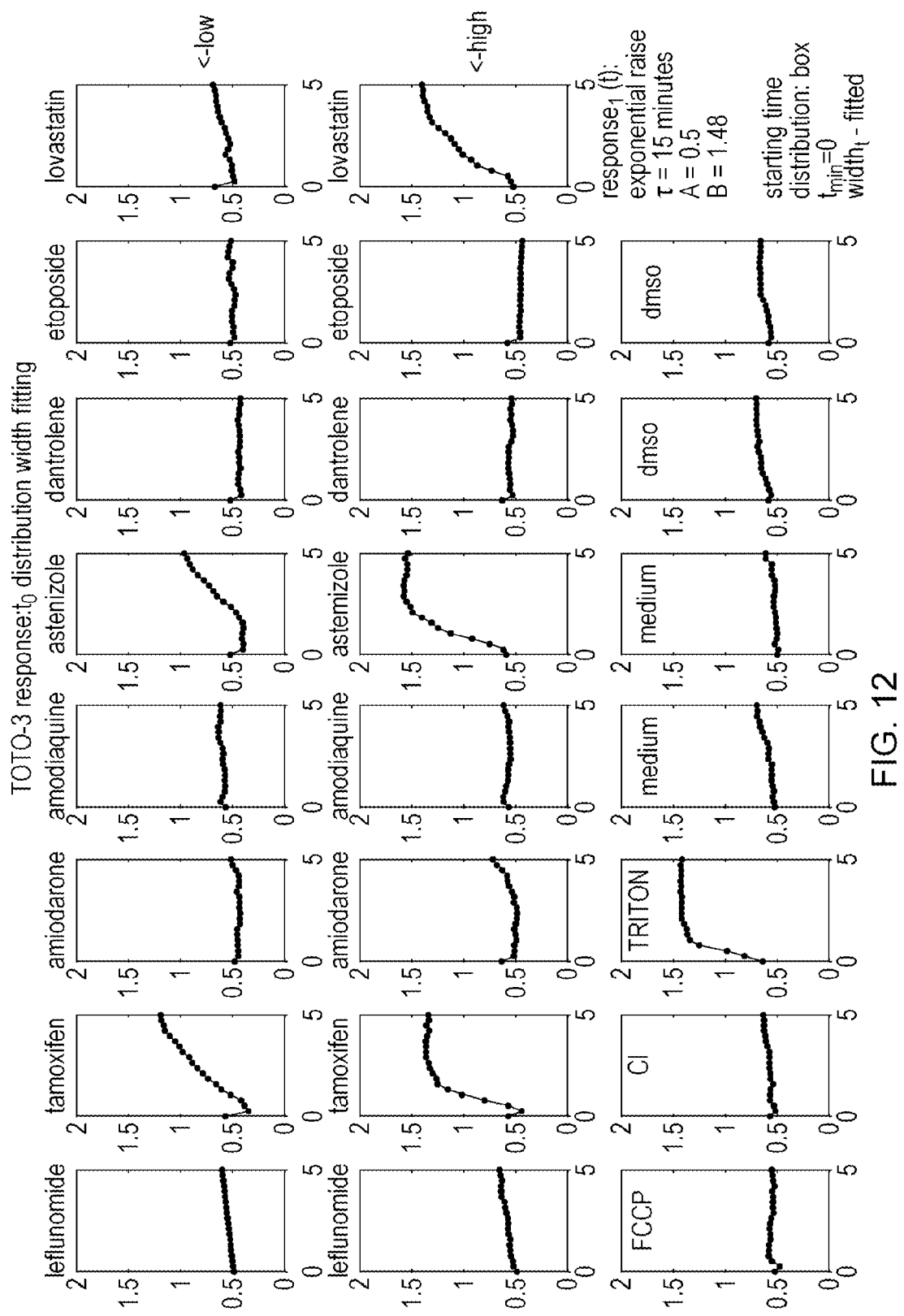
FIG. 12 shows the response of FIG. 11 with fitted data curves.

FIG. 12 shows the response of FIG. 11 with fitted data curves. Data fitting was performed using a $response_1(t)$ function having an exponential rising shape. τ was equal to 15 minutes, A=0.5 and B=1.48. The starting time distribution was box shaped with $t_{min}$=0 and width$_t$–fitted.

Figure 13:
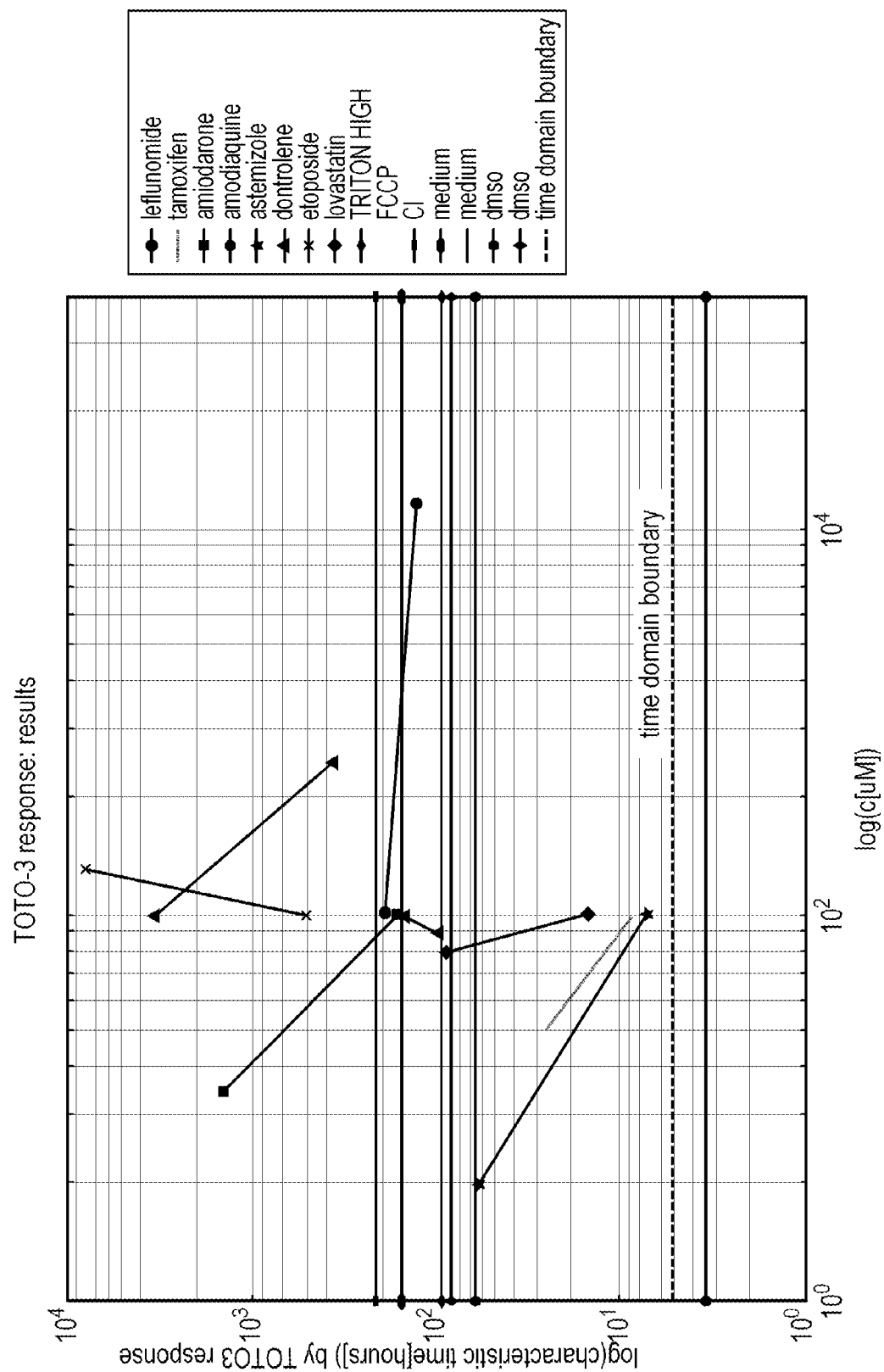
FIG. 13 shows an experimental TOTO-3 concentration response.

FIG. 13 shows an experimental TOTO-3 concentration response showing the logarithm of characteristic time (in hours) by TOTO-3 response (y-axis) as a function of logarithm of concentration (micromoles) (x-axis) for various drug compounds.

FIGS. 11 to 13 demonstrate the utility of the analytical method since it allows for the classifying of drugs quantitatively by their mode of action in terms of fast/slow responders. In particular, it can be seen that three toxic drugs (astemizole, tamoxifen and lovastatin) can be identified by this method as responding faster than controls. These Figures also show that increasing concentration of these drugs makes the response even faster.

SECOND EXAMPLE

The second example analyzed a mitochondrial marker (TMRM) response. This analysis did not take into account stochastic effects and was therefore reduced to the usual fitting procedure for the FOV-averaged response. It was assumed that all cells started reacting immediately after drug addition. The reaction of a mitochondrial potential to a perturbation (i.e. a drug) is considered to be potentially very diverse.

The form of analytical expression used for $response_1(t)$ was as follows:

$$f(t) = A\left(1 + \frac{K}{|K|} z^{\alpha} e^{-z}\right) + \text{range}(1 - e^{-z}) \qquad \text{Equation 16}$$

with limits $f(0)=A$, $f(\infty)=A+\text{range}$
and where $$z = \frac{t}{\tau}, \tau = |K|^{-\frac{1}{\alpha}}$$

where range, K and α are three fitting parameters, and A is fixed being assigned after inspection of the response on unperturbed cells (i.e. as a baseline).

The expression defined in Equation 16 above is very flexible, and uses as a fitting parameter the single time scale ("τ"), amplitude ("range") and another parameter ("α") for controlling response nonlinearity.

Figure 14:
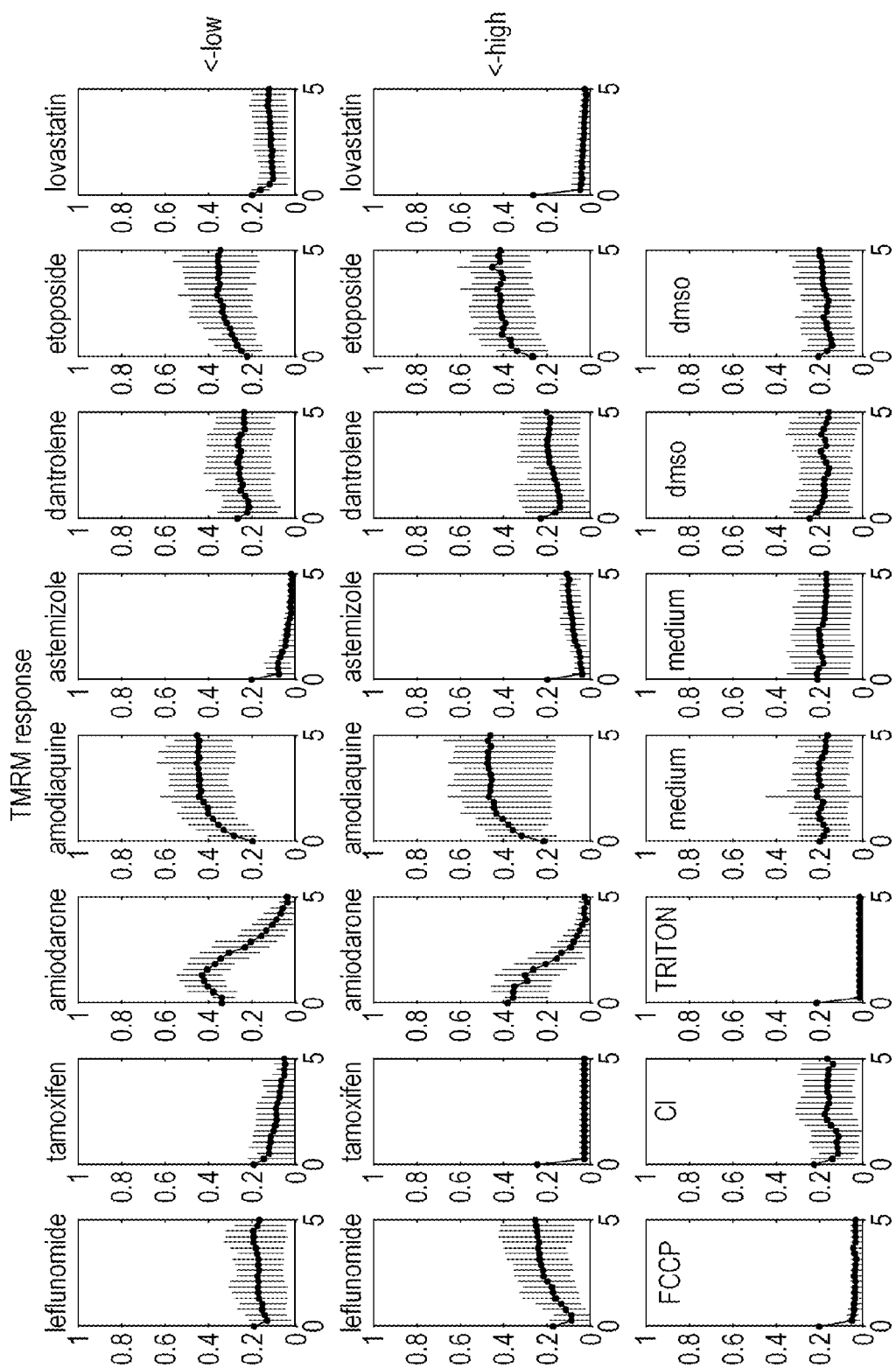
FIG. 14 shows a raw time-dependent TMRM response.

FIG. 14 shows the raw time-dependent TMRM response. The TMRM response was taken for two values of drug concentration, denoted "high" and "low". The bottom panel shows the response when treated with various control treatments (i.e. FCCP: p-trifluoromethoxy carbonyl cyanide phenyl hydrazone; CI: calcium ionophore A23187; Triton: Triton-X-100; Medium: culture medium; DMSO: dimethylsulphoxide).

Figure 15:
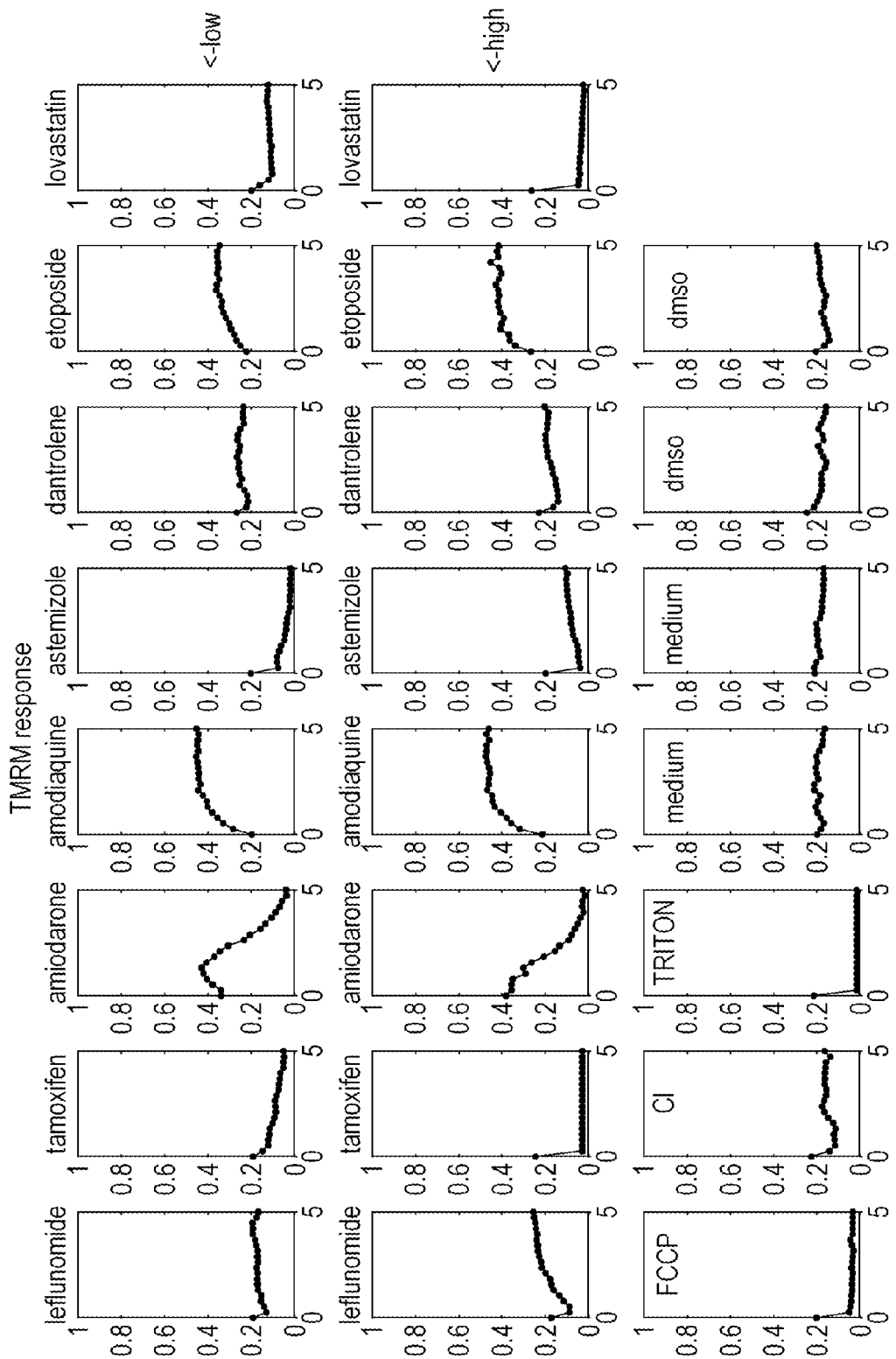
FIG. 15 shows the response of FIG. 14 with fitted data curves.

FIG. 15 shows the response of FIG. 14 with fitted data curves. Data fitting was performed using the technique discussed in relation to Equation 16, above.

Figure 16:
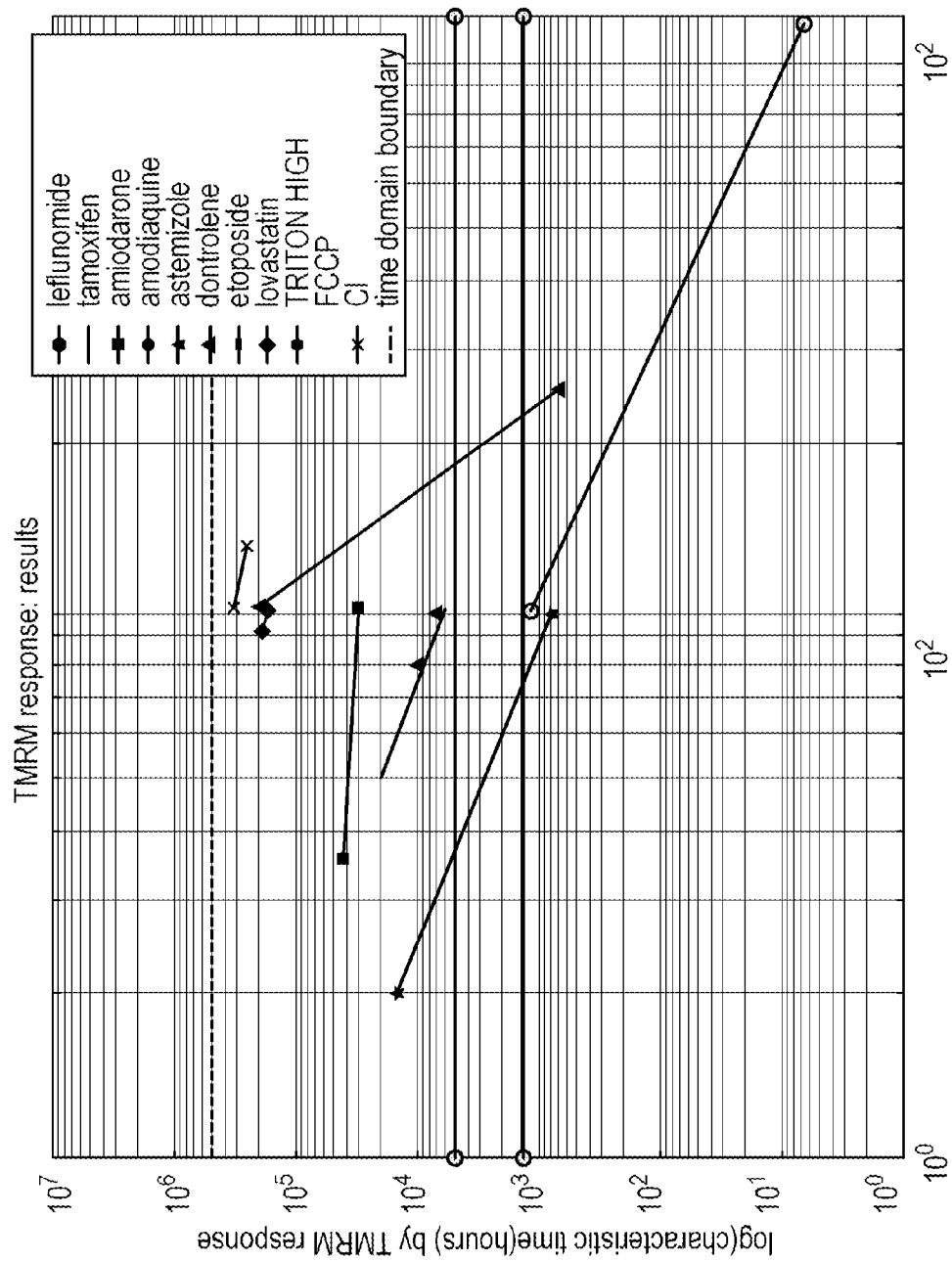
FIGS. 16 and 17 show concentration dependencies for the TMRM responses for two values of drug concentration.
Figure 17:
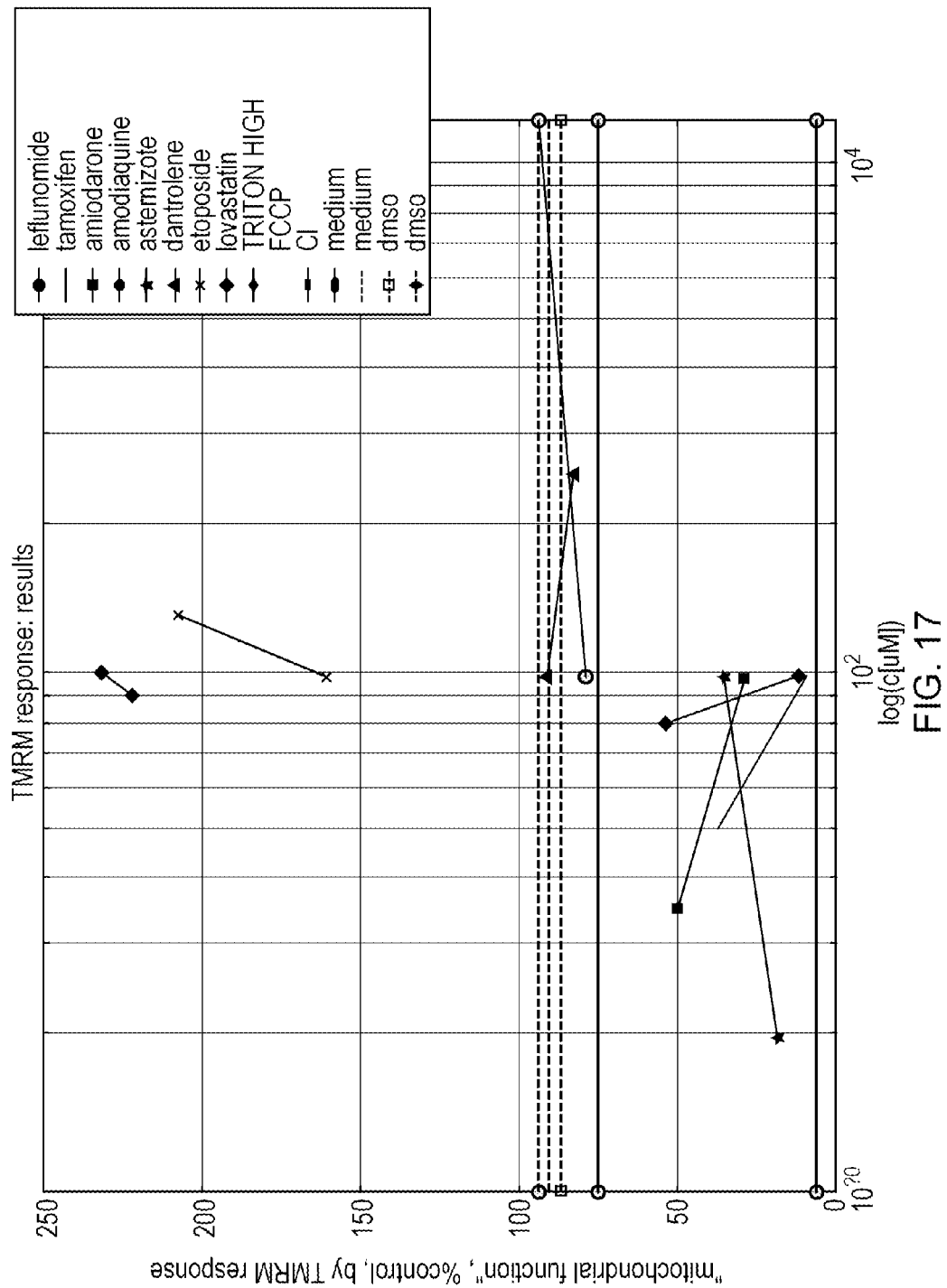

FIGS. 16 and 17 show rudimentary "concentration dependencies" (plotted for the two values of drug concentration, "high" and "low") of the two important parameters "range" and "τ".

FIGS. 14 to 17 demonstrate the utility of the fitting method since they allow for the classification of drugs quantitatively by their mode of action i.e. in terms of fast/slow and suppressing/stimulating characteristics. The latter characteristic is apparent and is an example of the hormesis exhibited by etoposide and amodiaquine (i.e. data >100% of the TMRM level, showing raised mitochondrial activity). The majority of the other drugs appear to suppress mitochondrial function and the drugs leflunomide and dantrolene have no effect. For all cases studied, analysis of the characteristic time "τ" as a parameter indicates that increasing drug concentration results in a faster TMRM response.

Various techniques may be used to provide embodiments of the present invention, such as, for example:
1) direct fitting, which can be applied to many time dependencies recorded from cells with the help of cell tracking, or to FOV-averaged responses;
2) indirect fitting, by comparing measured and modelled FOV-averaged responses in the time domain; and/or
3) indirect fitting, by comparing measured and modelled distributions of the FOV responses at certain time points.

The latter two techniques might use a "$t_0$ distribution" methodology.

Further analysis options may also or alternatively include:
1) concentration dependencies of fitting parameters;
2) perturbations (or drugs) might be classified in the space defined by fitting parameters; and/or
3) responses of different markers can be ranked according to their characteristic times.

As previously mentioned, alternative possible methods exist for constructing the $response_1(t)$ model curve(s) used to represent the basic dynamic cellular event(s), compared to those explicitly described herein.

In particular, two cases of $response_1(t)$ curve generation that might be beneficial for such simulations include:
1) A bistable assay, i.e. in this system a composite response originates from two basic $response_1(t)$ curves. As an example one can fit the mixture of two responses with different timings (providing "high" and "low" levels of signal at $t=\infty$). In this case, bimodal response distributions are possible. Such a method can be applied to stochastic simulations.
2) Generating the $response_1(t)$ with the help of intra-cellular kinetics modelling, for example by the ordinary differential equation (ODE) formalism. In this case, the set of parameters controlling the shape of the $response_1(t)$ curves coincide with parameters from the biochemical kinetic model.

Such extensions of the method using bistable responses, measurement noise introduction and/or ODE-modelled responses can, for example, be incorporated into a GE IN Cell Investigator software analysis tool.

Various aspects and embodiments of the present invention may thus be used to perform virtual experimentation based upon one or more of: temporal multi-scale responses, single cell responses, transient responses, characteristic times, response amplitudes, response starting times, stochastic fitting, bistability, ODE analysis, etc. In various embodiments a virtual assay model (VAM) can be used with feedback in order to improve VAM accuracy. Various techniques incorporating stochastic data and/or stochastic analysis may also be used.

In various embodiments of the present invention, image acquisition may be provided to obtain actual images. This may be done in real-time or by using off-line processing to perform image analysis in order to compare VAM output data to measured responses.

Therefore whilst the present invention has been described in accordance with various aspects and preferred embodiments, it is to be understood that the scope of the invention is not considered to be limited solely thereto and that it is the Applicant's intention that all variants and equivalents thereof also fall within the scope of the appended claims.

REFERENCES

1. WO 2005/007744 (GENE NETWORK SCIENCES, INC.)
2. WO 02/099736 (PHYSIOME SCIENCES, INC.)
3. US 2003/0018457 (PHYSIOME SCIENCES, INC.)
4. P. J. O'Brien, et al., "High Concordance of Drug-Induced Human Hepatotoxicity with In-Vitro Cytotoxicity Measured in a Novel Cell-Based Model Using High Content Screening," Archives of Toxicology (2006), ISSN 0340-5761, vol. 80, no. 9, pp. 580-604, DOI 10.1007/s00204-006-0091-3

Where permitted, the contents of the above-mentioned references are hereby also incorporated into this application by reference in their entirety.

The invention claimed is:

1. A system for automated cellular assay data analysis, the system comprising:
   a virtual assay module (VAM) operable to generate simulated images of cell responses to one or more stimuli, the generated simulated images being created using a stochastic model that simulates a stochastic process wherein behaviour is non-deterministic in that a next system state is determined both by predictable events of the stochastic process and by a random element;
   a comparator module operable to compare the actual and simulated images; and
   an analysis module operable to quantify the differences between phenotypes represented by the actual and simulated images.

2. The system of claim 1, wherein the analysis module is further operable to provide feedback to adjust the VAM in accordance with the quantified differences such that the phenotypes of the actual and simulated images converge.

3. The system of claim 1, wherein the analysis module is further operable to quantify temporally the differences between the phenotypes represented by the actual and simulated images.

4. The system of claim 1, wherein the analysis module is further operable to apply stochastical fitting to quantify one or more response properties of a single cell's response to said one or more stimuli.

5. The system of claim 1, wherein
   the analysis module is further operable to apply phenomenological response fitting for a high-throughput screening (HTS) analysis.

6. The system of claim 1, wherein the analysis module is further operable to analyse heterogeneity of a multiple cellular system in response to said one or more stimuli to determine a heterogeneity measurement parameter.

7. The system of claim 1, wherein phenotypes are toxological phenotypes and the quantified differences are indicative of stimuli toxicity.

8. A method for automated biological cell assay data analysis, the method comprising:
   acquiring one or more actual cell images;
   creating one or more virtual assay model images using a stochastic model that simulates a stochastic process wherein behaviour is non-deterministic in that a next system state is determined both by predictable events of the stochastic process and by a random element;
   comparing at least one of the actual cell images to at least one of the virtual assay model images; and
   quantifying any differences identified by comparing actual and virtual assay model images to provide at least one difference parameter.

9. The method of claim 8, further comprising:
   modifying a virtual image model in dependence upon said at least one difference parameter; and
   recreating said one or more virtual assay model images using said modified virtual image model.

10. The method of claim 8, further comprising:
    iteratively providing feedback to adjust the virtual assay model so as to minimise the values of said at least one difference parameter in order that the phenotypes of the actual and virtual assay model images converge.

11. The method of claim 8, further comprising:
    temporally quantifying the differences between the phenotypes represented by the actual and virtual assay model images.

12. The method of claim 8, further comprising:
    applying stochastical fitting to quantify one or more response parameters for a single cell's response to one or more stimuli.

13. The method of claim 8, further comprising:
    applying phenomenological response fitting to a high-throughput screening (HTS) analysis.

14. The method of claim 8, further comprising:
    analysing heterogeneity of a multiple cellular system in response to one or more stimuli to determine a heterogeneity measurement parameter.

15. The method of claim 8, wherein phenotypes are toxological phenotypes and the quantified differences are indicative of stimuli toxicity.

* * * * *